United States Patent
Sugata (10) Patent No.: US 10,874,576 B2
(45) Date of Patent: Dec. 29, 2020

(54) GAIT STATE DETERMINATION APPARATUS, GAIT STATE DETERMINATION METHOD, AND WALKING TRAINING APPARATUS

(71) Applicant: TOYOTA JIDOSHA KABUSHIKI KAISHA, Toyota (JP)

(72) Inventor: Hikaru Sugata, Miyoshi (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 843 days.

(21) Appl. No.: 15/230,578

(22) Filed: Aug. 8, 2016

(65) Prior Publication Data

US 2017/0049660 A1 Feb. 23, 2017

(30) Foreign Application Priority Data

Aug. 17, 2015 (JP) .................. 2015-160697

(51) Int. Cl.
*A61H 3/00* (2006.01)
*A61H 1/02* (2006.01)
(Continued)

(52) U.S. Cl.
CPC ........... *A61H 3/008* (2013.01); *A61B 5/1038* (2013.01); *A61B 5/112* (2013.01); *A61F 2/70* (2013.01);
(Continued)

(58) Field of Classification Search
CPC .............. A61H 3/00–068; A61H 1/024; A61H 1/0244; A61H 1/0262; A61F 2/60;
(Continued)

(56) References Cited

U.S. PATENT DOCUMENTS

2005/0101448 A1 5/2005 He et al.
2010/0271051 A1* 10/2010 Sankai ................ A61B 5/1038
324/679

(Continued)

FOREIGN PATENT DOCUMENTS

| CN | 101862255 A | 10/2010 |
| EP | 2 500 007 A1 | 9/2012 |

(Continued)

*Primary Examiner* — Suba Ganesan
*Assistant Examiner* — Aren Patel
(74) *Attorney, Agent, or Firm* — Oblon, McClelland, Maier & Neustadt, L.L.P.

(57) ABSTRACT

A gait state determination apparatus includes: a foot attachment structure disposed in the walking assistance apparatus, the foot attachment structure to be attached to a foot of a user; a pressure detection device, disposed in the foot attachment structure, detecting a pressure exerted on a sole of the user; a pressure center calculation device successively calculating a center position of a pressure exerted on the sole during a gait motion of the user based on the pressure exerted on the sole detected by the pressure detection device; and motion determination device determining that it is a timing of a start of forward swinging of the leg to which the walking assistance apparatus is attached when the center position of the pressure calculated by the pressure center calculation devices is shifted from a position in a heel region of the sole to a toe region thereof, is disclosed.

6 Claims, 10 Drawing Sheets

(51) Int. Cl.
*A61B 5/11* (2006.01)
*A63B 24/00* (2006.01)
*A63B 21/00* (2006.01)
*A61B 5/103* (2006.01)
*A63B 22/02* (2006.01)
*A61F 2/70* (2006.01)
*A63B 69/00* (2006.01)
*A63B 71/06* (2006.01)
*A61B 5/00* (2006.01)
*A61F 2/50* (2006.01)

(52) U.S. Cl.
CPC .......... *A61H 1/024* (2013.01); *A61H 1/0244* (2013.01); *A61H 1/0262* (2013.01); *A61H 3/00* (2013.01); *A63B 21/00181* (2013.01); *A63B 22/02* (2013.01); *A63B 24/0087* (2013.01); *A61B 5/6812* (2013.01); *A61B 5/6829* (2013.01); *A61F 2002/5039* (2013.01); *A61F 2002/701* (2013.01); *A61F 2002/704* (2013.01); *A61H 2201/0176* (2013.01); *A61H 2201/0192* (2013.01); *A61H 2201/1215* (2013.01); *A61H 2201/1261* (2013.01); *A61H 2201/14* (2013.01); *A61H 2201/163* (2013.01); *A61H 2201/164* (2013.01); *A61H 2201/165* (2013.01); *A61H 2201/1621* (2013.01); *A61H 2201/1652* (2013.01); *A61H 2201/5007* (2013.01); *A61H 2201/5043* (2013.01); *A61H 2201/5048* (2013.01); *A61H 2201/5061* (2013.01); *A61H 2201/5071* (2013.01); *A61H 2230/80* (2013.01); *A63B 21/4007* (2015.10); *A63B 21/4009* (2015.10); *A63B 21/4011* (2015.10); *A63B 69/0057* (2013.01); *A63B 71/0622* (2013.01); *A63B 2024/0093* (2013.01); *A63B 2071/065* (2013.01); *A63B 2220/52* (2013.01)

(58) Field of Classification Search
CPC ... A61F 2/70; A63B 22/0242; A63B 69/0064; A63B 24/0087
USPC ............................................ 601/35; 600/595
See application file for complete search history.

(56) References Cited

U.S. PATENT DOCUMENTS

| | | | |
|---|---|---|---|
| 2011/0071442 A1* | 3/2011 | Park | A61H 1/0262 601/35 |
| 2011/0275043 A1 | 11/2011 | Liu | |
| 2012/0253234 A1 | 10/2012 | Yang et al. | |
| 2013/0137553 A1* | 5/2013 | Kim | A61H 1/024 482/69 |
| 2014/0058299 A1 | 2/2014 | Sankai et al. | |
| 2015/0045703 A1 | 2/2015 | Strausser et al. | |
| 2015/0141878 A1 | 5/2015 | Roy et al. | |
| 2016/0051859 A1* | 2/2016 | Nakashima | A61H 3/008 482/4 |

FOREIGN PATENT DOCUMENTS

| | | |
|---|---|---|
| JP | 2006-204730 A | 8/2006 |
| JP | 2009-106391 A | 5/2009 |
| JP | 2011-050451 A | 3/2011 |
| JP | 2012-81018 A | 4/2012 |
| JP | 2012-095793 A | 5/2012 |
| JP | 2014-184047 A | 10/2014 |
| JP | 2015-512287 A | 4/2015 |
| JP | 2015-223294 A | 12/2015 |
| JP | 2016-104057 A | 6/2016 |
| WO | WO 2013/142777 A1 | 9/2013 |

* cited by examiner

GAIT STATE DETERMINATION APPARATUS, GAIT STATE DETERMINATION METHOD, AND WALKING TRAINING APPARATUS

CROSS-REFERENCE TO RELATED APPLICATIONS

This application is based upon and claims the benefit of priority from Japanese patent application No. 2015-160697, filed on Aug. 17, 2015, the entire contents of which are incorporated herein by reference in entirety.

BACKGROUND OF THE DISCLOSURE 1. Field of the Disclosure

The present application relates to a gait state determination apparatus, a gait state determination method, and a walking training apparatus capable of determining a gate state of a user.

2. Description of Related Art

For example, the applicant of the present application has proposed a walking training apparatus including a walking assistance apparatus that is attached to a leg of a user and assists walking performed by the user (see Japanese Unexamined Patent Application Publication No. 2012-95793).

Here, assume a configuration in which first pulling means for pulling one of the walking assistance apparatus and a user's leg upward and forward, and second first pulling means for pulling one of the walking assistance apparatus and the user's leg upward and forward are further added, and the resultant force of the vertically-upward components of the pulling forces applied by the first and second pulling means is roughly equal to the weight of the walking assistance apparatus so that the load caused by the gravitational force of the walking assistance apparatus exerted on the user's leg is reduced. The present inventors have found that the following problem occurs in this configuration. That is, the timing of the start of swinging of a leg in walking is also the timing at which the user reverses his/her leg's motion from the backward motion to the forward motion. Therefore, the leg to which the walking assistance apparatus is attached receives the backward inertial force from the walking assistance apparatus at this reverse timing. However, although the above-described walking training apparatus reduces the load on user's walking caused by the gravitational force of the walking assistance apparatus, it does not reduce the above-described load caused by the inertial force. Therefore, an excessive load is exerted on the leg to which the walking assistance apparatus is attached at the start of swinging of that leg. Further, when the load caused by the gravitational force in the vertically-upward direction is reduced as in the above-described configuration, the inertial force in the vertical direction for raising the leg from the ground (lifting the leg upward), in addition to the backward inertial force, acts as a load on the leg.

Therefore, to reduce this load caused by the inertial force, it is preferred to accurately determine the start of swinging of the leg to which the walking assistance apparatus is attached and, for example, increase a pulling force applied by pulling means so as to reduce the inertial force at the start of swinging of the leg. However, in the above-described walking training apparatus, the start of swinging of the leg to which the walking assistance apparatus is attached is not determined and the above-described load is not reduced.

SUMMARY

The present disclosure has been made in view of the above-described problem and one of the main objects thereof is to provide a gait state determination apparatus, a gait state determination method, and a walking training apparatus capable of accurately determining the start of swinging of a leg to which a walking assistance apparatus is attached.

A first exemplary aspect of the present disclosure to achieve the aforementioned object s a gait state determination apparatus that determines a gait state of a user with a walking assistance apparatus attached to a leg of the user, the walking assistance apparatus being configured to assist the user to walk, the gait state determination apparatus including: a foot attachment structure disposed in the walking assistance apparatus, the foot attachment structure to be attached to a foot of the user, pressure detection means, disposed in the foot attachment structure, for detecting a pressure exerted on a sole of the user; pressure center calculation means for successively calculating a center position of a pressure exerted on the sole during a gait motion of the user based on the pressure exerted on the sole detected by the pressure detection means, and motion determination means for determining that it is a timing of a start of forward swinging of the leg to which the walking assistance apparatus is attached when the center position of the pressure calculated by the pressure center calculation means is shifted from a position in a heel region of the sole to a toe region thereof. According to this aspect, it is possible to accurately determine the start of swinging of the leg to which the walking assistance apparatus is attached.

In this aspect, the motion determination means may determine that it is the timing of the start of forward swinging of the leg to which the walking assistance apparatus is attached when the center position of the pressure is shifted from the heel region of the sole to the toe region thereof and remains in the toe region for a predetermined time or longer. According to this aspect, it is possible to determine the start of swinging of the leg in a stable state in which the center position of the pressure remains in the toe region for the predetermined time or longer. As a result, the start of forward swinging of the leg to which the walking assistance apparatus is attached can be determined more accurately.

Another exemplary aspect of the present disclosure to achieve the aforementioned object may be a gait state determination method for determining a gait state of a user with a walking assistance apparatus attached to a leg of the user, the walking assistance apparatus being configured to assist the user to walk, the gait state determination method including: detecting a pressure exerted on a sole of a foot of the leg to which the walking assistance apparatus is attached, successively calculating a center position of a pressure exerted on the sole during a gait motion of the user based on the pressure exerted on the sole detected; and determining that it is a timing of a start of forward swinging of the leg to which the walking assistance apparatus is attached when the calculated center position of the pressure is shifted from a position in a heel region of the sole to a toe region thereof. According to this aspect, it is possible to accurately determine the start of swinging of the leg to which the walking assistance apparatus is attached.

Another exemplary aspect of the present disclosure may be a walking training apparatus including: the above-described gait state determination apparatus, first pulling means for pulling the leg upward and forward directly or through the walking assistance apparatus; control means for controlling the first pulling means so that a vertically-upward component of a pulling force applied by the first pulling means reduces a weight of the walking assistance apparatus; and in which the control means makes the first pulling means generate an additional pulling force in addition to the pulling force when it is determined by the motion determination means that it is the timing of the start of forward swinging of the leg. According to this aspect, it is possible to reduce the inertial force at the start of swinging of the leg, which is accurately determined, by increasing the pulling force applied by the first pulling means at the start of swinging of the leg.

Another exemplary aspect of the present disclosure may be gait state determination apparatus including: a foot attachment structure disposed in the walking assistance apparatus, the foot attachment structure to be attached to a foot of the user; a pressure sensor disposed in the foot attachment structure, the pressure sensor to detect a pressure exerted on a sole of the user; and circuitry configured to: successively calculate a center position of a pressure exerted on the sole during a gait motion of the user based on the pressure exerted on the sole detected by the pressure sensor, and determine that it is a timing of a start of forward swinging of the leg to which the walking assistance apparatus is attached when the center position of the pressure calculated is shifted from a position in a heel region of the sole to a toe region thereof.

In this aspect, the circuitry may be further configured to determine that it is the timing of the start of forward swinging of the leg to which the walking assistance apparatus is attached when the center position of the pressure is shifted from the heel region of the sole to the toe region thereof and remains in the toe region for a predetermined time or longer.

Another exemplary aspect of the present disclosure may be a walking training apparatus including: the above-described gait state determination apparatus; and a first pulling mechanism to pull the leg upward and forward directly or through the walking assistance apparatus, and in which the circuitry is further configured to: control the first pulling mechanism so that a vertically-upward component of a pulling force applied by the first pulling mechanism reduces a weight of the walking assistance apparatus, and make the first pulling mechanism generate an additional pulling force in addition to the pulling force when it is determined by the circuitry that it is the timing of the start of forward swinging of the leg.

According to the present disclosure, it is possible to provide a gait state determination apparatus, a gait state determination method, and a walking training apparatus capable of accurately determining the start of swinging of a leg to which a walking assistance apparatus is attached.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF THE EXEMPLARY EMBODIMENTS

Exemplary embodiments according to the present disclosure are explained hereinafter with reference to the drawings.

Figure 1:
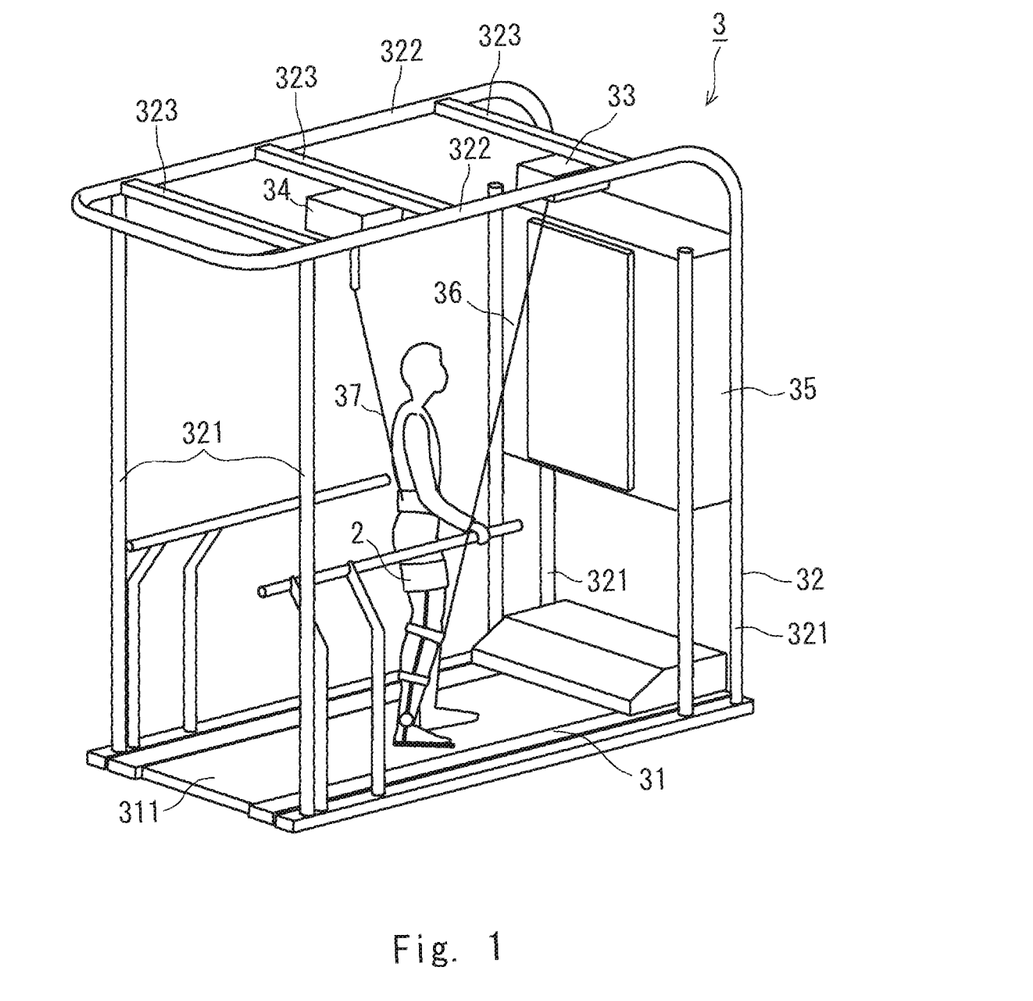
FIG. 1 is a perspective view showing a schematic configuration of a walking training apparatus according to an exemplary embodiment of the present disclosure.

FIG. 1 is a perspective view showing a schematic configuration of a walking training apparatus according to an exemplary embodiment of the present disclosure. A walking training apparatus according to this exemplary embodiment is, for example, an apparatus by which a user such as a patient having hemiplegia caused by a stroke does a walking training. The walking training apparatus includes a walking assistance apparatus 2 attached to the user's leg and a training apparatus 3 by which the user does a walking training.

Figure 2:
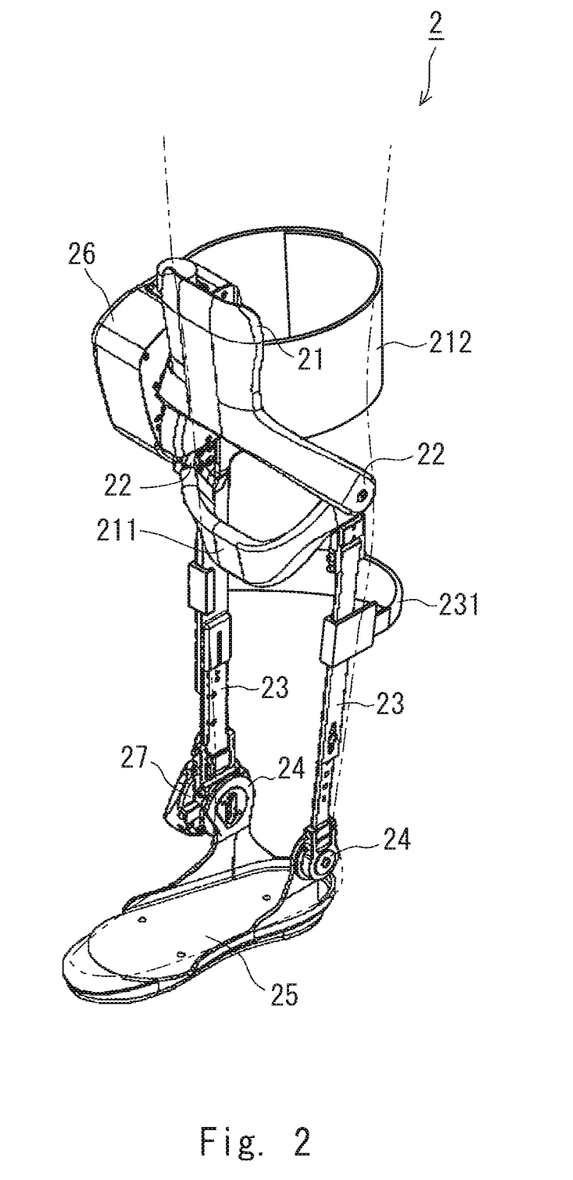
FIG. 2 is a perspective view showing a schematic configuration of a walking assistance apparatus.

The walking assistance apparatus 2 is, for example, attached to a diseased leg of a user who does a walking training and assists walking of the user (FIG. 2). The walking assistance apparatus 2 includes an upper thigh frame 21, a lower thigh frame 23 connected to the upper thigh frame 21 through a knee joint part 22, a sole frame (a specific example of the foot attachment part) 25 connected to the lower thigh frame 23 through an ankle joint part 24, a motor unit 26 that rotationally drives the knee joint part 22, and an adjustment mechanism 27 that adjusts the movable range of the ankle joint part 24. Note that the above-described configuration of the walking assistance apparatus 2 is merely an example and the configuration of the walking assistance apparatus 2 is not limited to such an example. For example, the walking assistance apparatus 2 may include another motor unit that rotationally drives the ankle joint part 24.

Figure 3:
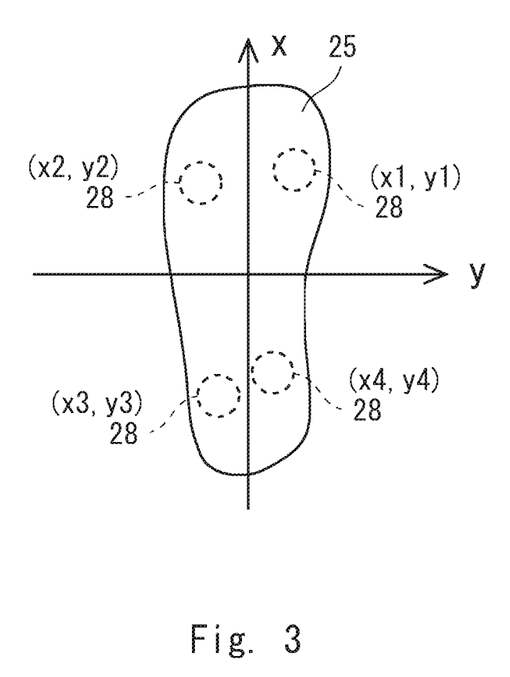
FIG. 3 shows pressure sensors provided on a toe side and a heel side of a sole frame.

A pair of pressure sensors 28 is provided on each of a toe side and a heel side of the sole frame 25 (FIG. 3). The pressure sensors 28 are a specific example of the pressure detection means. Each of the pressure sensors 28 may be, for example, a vertical pressure sensor that detects a vertical pressure exerted on the sole of the sole frame 25. Note that the number and the positions of the pressure sensors 28 provided in the sole frame 25 may be arbitrarily determined, provided that they can accurately determine the center of the pressure exerted on the sole. For example, at least three pressure sensors 28 need to be disposed and they should not be arranged in a straight line. For the pressure center determination, the pressure sensors 28 are preferably disposed so that the area of a polygon that is formed by connecting the disposed pressure sensors 28 by straight lines becomes larger. In this way, the pressure center can be accurately detected over a wide area.

The walking assistance apparatus 2 is a specific example of the pressure center calculation means and successively calculates the position of the COP (Center Of Pressure) (hereinafter also referred to as the "COP position") of the sole during the user's gait motion based on the pressure on the sole of the sole frame 25 detected by the pressure sensors 28.

For example, as shown in FIG. 3, the center position of the sole of the sole frame 25 is defined as die origin of a two-dimensional XY-coordinate system, and the positions of a first pressure sensor 28 on a toe side, a second pressure sensor 28 on the toe side, a third pressure sensor on a heel side, and a fourth pressure sensor on the heel side are expressed as (x1, y1), (x2, y2), (x3, y3) and (x4, y4), respectively. Further, the magnitudes of pressures exerted on the first to fourth pressure sensors 28 are represented by Ni (i=1 to 4). For example, die walking assistance apparatus 2 calculates a COP position ($x_{COP}$, $y_{COP}$) by using the below-shown expression.

$$x_{COP} = \frac{\sum_{i=1}^{4} N_i x_i}{\sum_{i=1}^{4} N_i}$$ [Expression 1]

$$y_{COP} = \frac{\sum_{i=1}^{4} N_i y_i}{\sum_{i=1}^{4} N_i}$$

The above-described method for calculating a COP position is merely an example and the calculation method is not limited to this example. For example, instead of providing the pressure sensors 28, a pressure distribution sensor that detects a pressure distribution on the sole of the sole frame 25 may be provided on the sole of the sole frame 25. The walking assistance apparatus 2 may calculate a COP position based on a pressure distribution on the sole calculated by the pressure distribution sensor.

The upper thigh frame 21 is attached to the upper thigh of the user's leg and the lower thigh frame 23 is attached to the lower thigh of the user's leg. The upper thigh frame 21 is, for example, equipped with an upper thigh harness 212 for fixing the upper thigh. The upper thigh frame 21 is equipped with a horizontally-extending and horizontally-long first frame 211 for connecting with a wire 36 of a first pulling unit 33 (which is described later). The lower thigh frame 23 is equipped with a horizontally-extending and horizontally-long second frame 231.

Note that the above-described connecting part of the first pulling unit 33 is merely an example and the connection of the first pulling unit 33 is not limited to such an example. For example, the wire 36 of the first pulling unit 33 may be connected to the upper thigh harness 21 and the pulling point of the first pulling unit 33 can be disposed at an arbitrary position in the walking assistance apparatus 2.

The motor unit 26 rotationally drives the knee joint part 22 according to the walking motion of the user and thereby assists the walking of the user. Note that the above-described configuration of the walking assistance apparatus 2 is merely an example and the configuration of the walking assistance apparatus 2 is not limited to such an example. Any walking assistance apparatus capable of being attached to the user's leg and assisting walking of the user can be applied.

The training apparatus 3 includes a treadmill 31, a frame main body 32, first and second pulling units 33 and 34, and a control device 35. The treadmill 31 rotates a ring-shaped belt 311. The user gets on the belt 311 and walks on the belt 311 according to the movement of the belt 311. By doing so, the user does a walking training.

The frame main body 32 includes two pairs of pillar frames 321 vertically disposed on the treadmill 31, a pair of lengthwise frames 322 extending in the lengthwise direction and connected to respective pillar frames 321, and three crosswise frames 323 extending in the crosswise direction and connected to each of the lengthwise frames 322. Note that the configuration of the above-described frame main body 32 is not limited to this example. Any frame structure can be adopted for the frame main body 32, provided that the first and second pulling units (which are described later) can be appropriately fixed to the frame main body 32.

In the front crosswise frame 323, the first pulling unit 33 that pulls the wire 36 upward and forward is provided. The first pulling unit 33 is a specific example of the first pulling means. The first pulling unit 33 includes, for example, a mechanism for winding up and back the wire 36, a motor that drives the mechanism, and so on. One end of the wire 36, which is pulled by the first pulling unit 33, is connected to the walking assistance apparatus 2. The first pulling unit 33 pulls the walking assistance apparatus 2 upward and forward through the wire 36.

The vertically-upward component of the pulling force applied by the first pulling unit 33 supports the weight of the walking assistance apparatus 2. The horizontally-forward component of the pulling force applied by the first pulling unit 33 assists the start of swinging o the leg. In this way, the walking load of the user in the walking training can be reduced.

The second pulling unit 34 is disposed in the rear crosswise frame 323 and pulls a wire 37 upward. One end of the wire 37 is connected to, for example, a belt attached to at or near the user's waist. The second pulling unit 34 includes, for example, a mechanism for winding up and back the wire 37, a motor that drives the mechanism, and so on. The second pulling unit 34 pulls the user's waist upward through the wire 37. In this way, the load on the user caused by the weight of the user himself/herself can be reduced. Each of the first and second pulling units 33 and 34 is connected to the control device 35 through a wiring line or the like.

The control device 35 controls each of the pulling forces applied by the first and second pulling units 33 and 34, the driving of the treadmill 31, and the walking assistance apparatus 2. For example, the control device 35 is formed by hardware mainly using a microcomputer including a CPU (Central Processing Unit) that performs arithmetic processing, control processing, and so on, a ROM (Read Only Memory) that stores an arithmetic program, a control program and so on to be executed by the CPU, a RAM (Random Access Memory) that stores various data and so on, and an interface unit (I/F) that externally receives and outputs signals. The CPU, the ROM, the RAM, and the interface unit are connected with each other through a data bus or the like.

Figure 4:
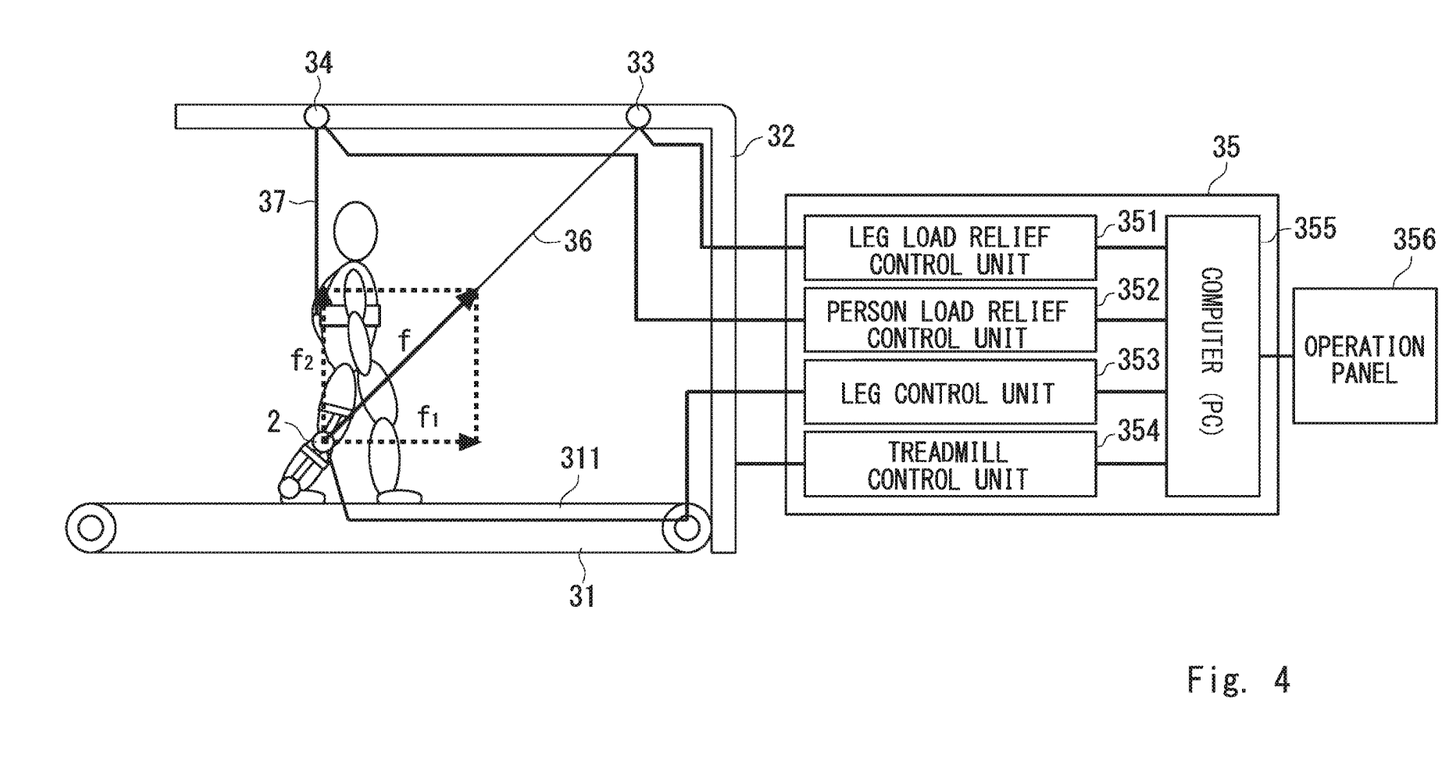
FIG. 4 is a block diagram showing a schematic system configuration of a control device according to an exemplary embodiment of the present disclosure.

FIG. 4 is a block diagram showing a schematic system configuration of the control device according to this exemplary embodiment.

The control device 35 includes, for example, a leg load relief control unit 351 that controls the first pulling unit 33, a person load relief control unit 352 that controls the second pulling unit 34, a leg control unit 353 that controls the walking assistance apparatus 2, a treadmill control unit 354 that controls the treadmill 31, a computer or a PC (Personal Computer) 355 that controls these units, and an operation panel 356 for operating the computer 355. The operation panel 356 displays information such as a training instruction, a training menu, and training information (such as walking speed and biological information). The operation panel 356 is formed, for example, as a touch panel, and a user can enter various types of information (pulling forces applied by the first and second pulling units 33 and 34) through the operation panel 356.

Incidentally, the timing of the start of swinging of a leg in the user's gait motion is also the timing at which the user reverses his/her leg's motion from the backward motion to the forward motion. Therefore, the leg to which the walking assistance apparatus is attached receives the backward inertial force from the walking assistance apparatus and hence a load is exerted on the leg at this reverse timing. Further, when the user lifts his/her leg upward, the downward inertial force also acts as a load that is caused as the user starts to swing the leg.

Therefore, to reduce this load caused by the inertial force, it is preferred to accurately determine the start of swinging of the leg to which the walking assistance apparatus is attached and increase a pulling force applied by the pulling means so as to reduce the inertial force at the start of swinging of the leg.

For this purpose, in this exemplary embodiment, attention is paid to an ergonomic characteristic that when a human is walking, the COP position is shifted from a heel region to a toe region during a period from when the foot is landed to when the foot starts swinging. By using this ergonomic characteristic, the start of swinging of the foot is accurately determined. That is, in a gait state determination apparatus according to this exemplary embodiment, a pressure exerted on the sole of the sole frame 25 of the walking assistance apparatus 2 is detected and a COP position on the sole is calculated based on the detected pressure on the sole. Then, when the calculated COP position is shifted from a position in a heel region of the sole to a toe region thereof, it is determined that it is a timing of a start of forward swinging of the leg to which the walking assistance apparatus 2 is attached. In this way, the start of swinging of the leg to which the walking assistance apparatus 2 is attached can be accurately determined. Further, it is possible to reduce the inertial force at the start of swinging of the leg, which is accurately determined, by increasing the pulling force f applied by the first pulling unit 33 and thereby generating an additional pulling force at the start of swinging of the leg.

Figure 5:
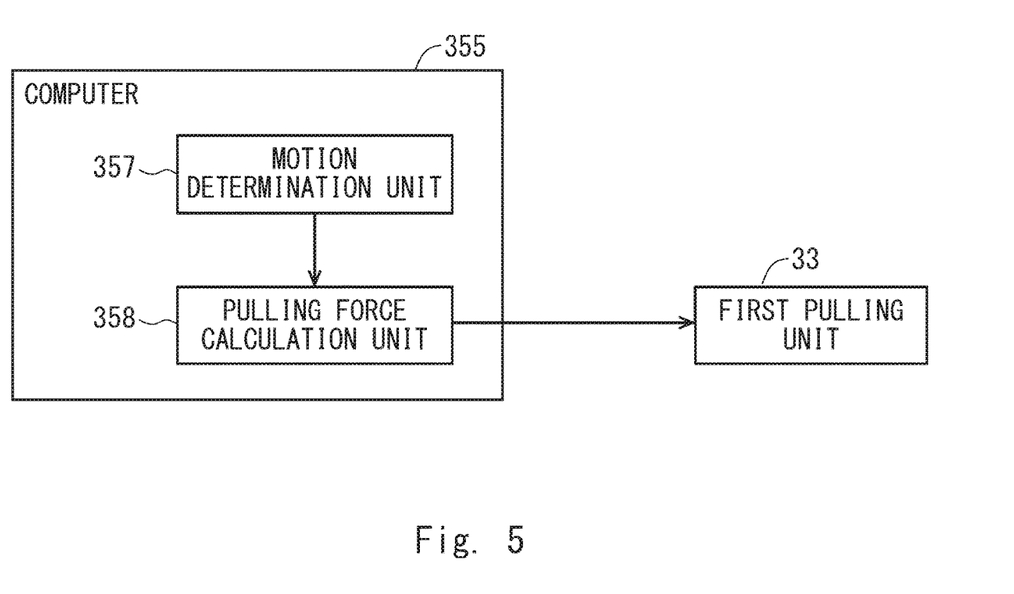
FIG. 5 is a block diagram showing a schematic system configuration of a computer according to an exemplary embodiment of the present disclosure.

FIG. 5 is a block diagram showing a schematic system configuration of a computer according to this exemplary embodiment. A computer 355 according to this exemplary embodiment includes a motion determination unit 357 that determines the start of swinging of a leg to which the walking assistance apparatus 2 is attached and a pulling force calculation unit 358 that increases the pulling force f applied by the first pulling unit 33 at the start of swinging of the leg.

The motion determination unit 357 is a specific example of the motion determination means. The motion determination unit 357 determines whether or not the COP position calculated by the walking assistance apparatus 2 is shifted from the heel region to the toe region of the sole of the sole frame 25 and thereby determines the start of forward swinging of the leg to which the walking assistance apparatus 2 is attached.

Next, a gait state determination method for accurately determining a start of forward swinging of a leg to which a walking assistance apparatus is attached is explained in detail.

Figure 6:
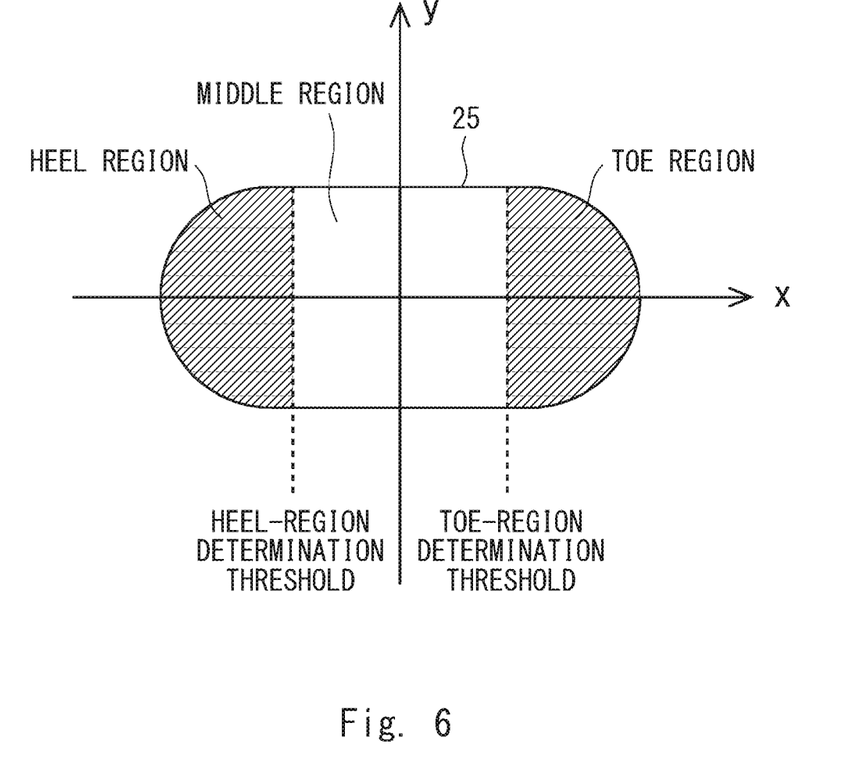
FIG. 6 shows a toe region, a middle region, and a heel region of a sole.

For example, as shown in FIG. 6, an XY-coordinate system in which the center of the sole of the sole frame 25 is defined as the origin of the coordinate system is defined. Then, each of a toe region, a middle region, and a heel region is defined on the sole in the XY-coordinate system. On the sole, a region whose x-coordinate value is equal to or greater than a toe-region determination threshold is the toe region (a hatched area). A region whose x-coordinate value is equal to or smaller than a heel-region determination threshold is the heel region (another hatched area). A region whose x-coordinate value is greater than the heel-region determination threshold and smaller than the toe-region determination threshold (i.e., a region between the toe region and the heel region) is the middle region. Note that the above-described toe-region determination threshold and heel-region determination threshold are experimentally obtained in advance, for example, and stored in the aforementioned ROM, the RAM, or the like. Further, the toe-region determination threshold and the heel-region determination threshold can be arbitrarily defined/changed by a user through, for example, the operation panel 356 or the like.

The motion determination unit 357 determines that the user has started swinging his/her leg to which the walking assistance apparatus 2 is attached forward when, for example, the COP position calculated by the walking assistance apparatus 2 moves from the heel region to the middle region and then enters the toe region in the above-described XY-coordinate system.

Figure 7:
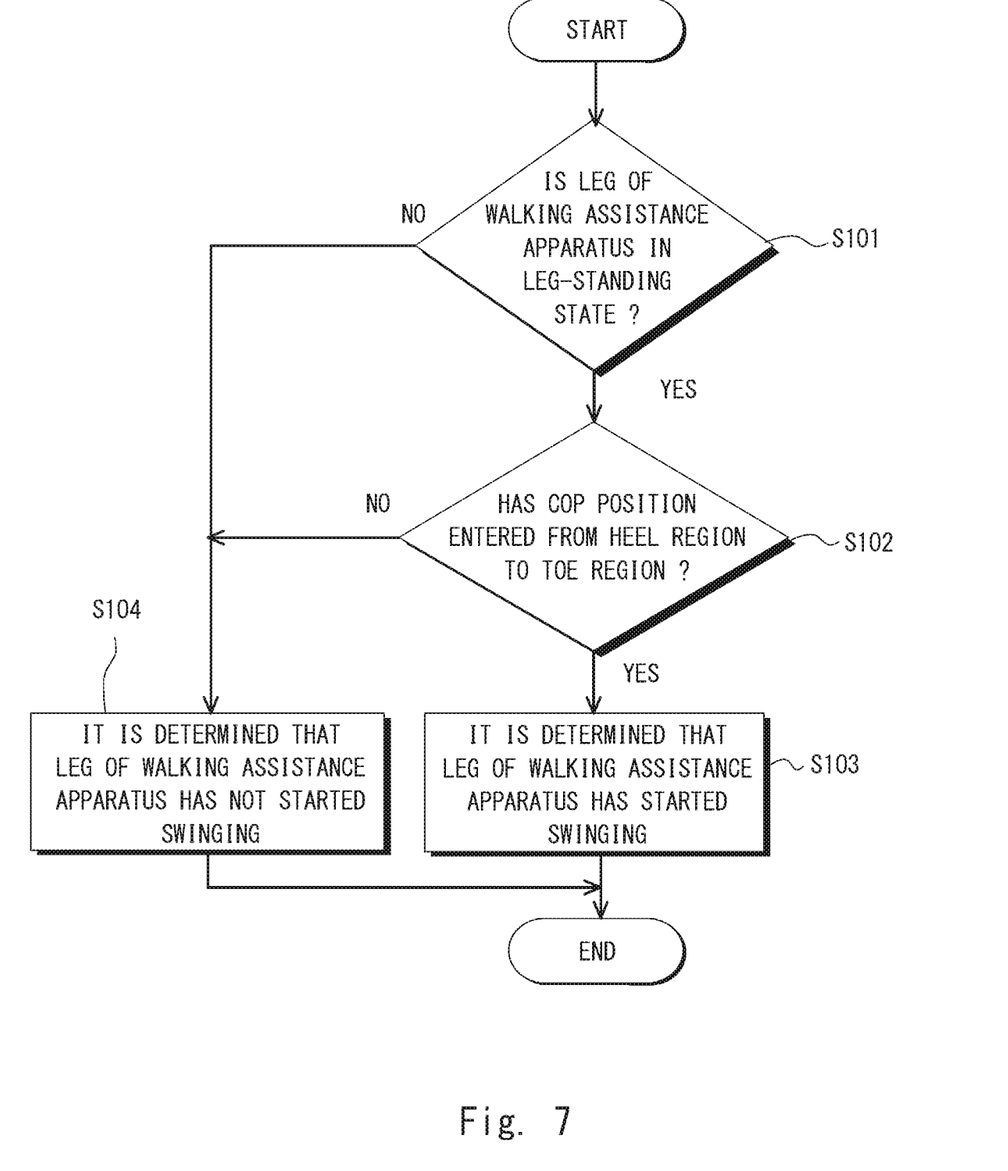
FIG. 7 is a flowchart showing an example of a determination flow according to a gait state determination method.

FIG. 7 is a flowchart showing an example of a determination flow according to the gait state determination method.

The motion determination unit 357 determines whether or not the leg to which the walking assistance apparatus 2 is attached is in a leg-standing state based on the pressure on the sole of the sole frame 25 detected by the pressure sensors 28 of the walking assistance apparatus 2 (step S101).

When the motion determination unit 357 determines that the leg to which the walking assistance apparatus 2 is attached is in the leg-standing state (Yes at step S101), the motion determination unit 357 determines whether or not the COP position $x_{cop}$ has changed from a value smaller than the heel-region determination threshold to a value equal to or greater than the toe-region determination threshold (i.e., whether or not the COP position has moved from the heel region and entered the toe region) (step S102). On the other hand, when the motion determination unit 357 determines that the leg to which the walking assistance apparatus 2 is attached is not in the leg-standing state (i.e., is in a leg-idling state) (No at step S101), the motion determination unit 357 proceeds to a later-described step S104.

Figure 8:
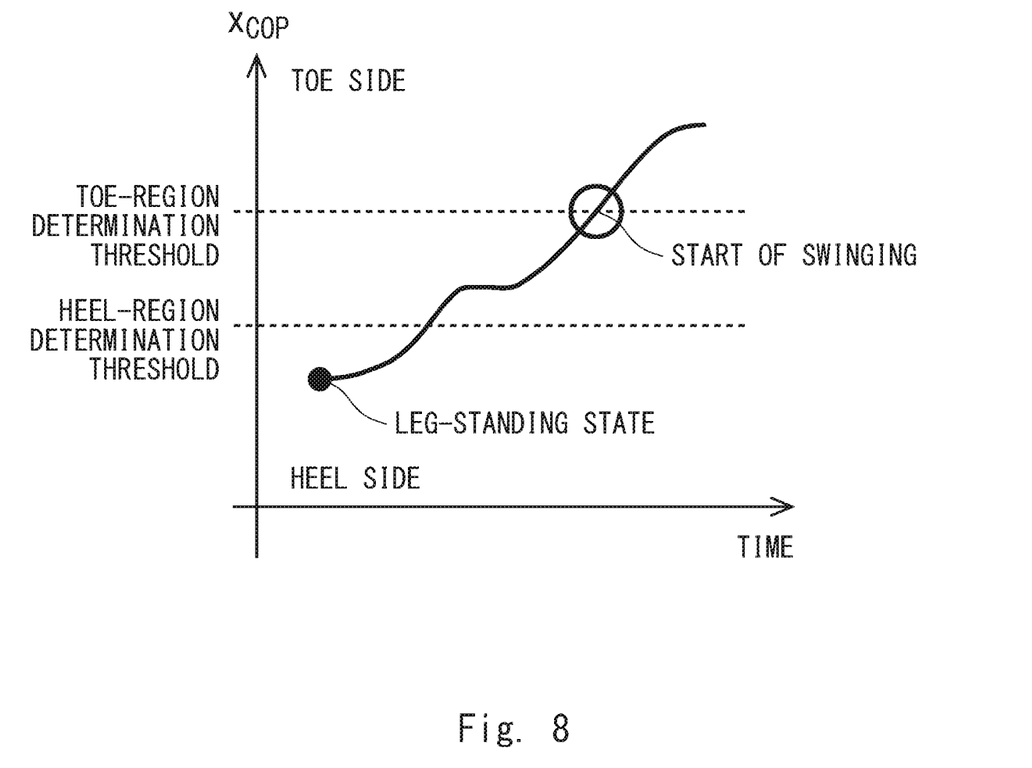
FIG. 8 shows an example of a timing of a start of swinging of a leg.

For example, as shown in FIG. 8, when the motion determination unit 357 determines that the COP position $x_{cop}$ has changed from a value smaller than the heel-region determination threshold to a value equal to or greater than the toe-region determination threshold (Yes at step S102), the motion determination unit 357 determines that the user has started swinging his/her leg to which the walking assistance apparatus 2 is attached forward (step S103). On the other hand, when the motion determination unit 357 determines that the COP position $x_{cop}$ has not changed from a value smaller than the heel-region determination threshold to a value equal to or greater than the toe-region determination threshold (No at step S102), the motion determination unit 357 determines that the user has not started swinging his/her leg to which the walking assistance apparatus 2 is attached forward (step S104).

Note that the motion determination unit 357 may determine that the user has started swinging his/her leg to which the walking assistance apparatus 2 is attached forward when the COP position calculated by the walking assistance apparatus 2 has moved from the heel region and entered the toe region, and remained in the toe region for a predetermined time or longer. For example, there are cases where the COP position is unstable because the COP position randomly drifts or vibrates such as a case where the user walks in a swinging manner. Even in such cases, it is possible to determine the start of swinging of the leg in a stable state in which the COP position has moved from the heel region and entered the toe region, and remained in the toe region for the predetermined time or longer. In this way the start of forward swinging of the leg to which the walking assistance apparatus 2 is attached can be determined more accurately. Note that the aforementioned predetermined time is determined, for example, according to the sensor characteristic of the pressure sensor and/or the gait state of the user in advance, and stored in the ROM, the RAM, or the like. Further, the aforementioned predetermined time can be arbitrarily defined/changed by a user through, for example, the operation panel 356 or the like.

Figure 9:
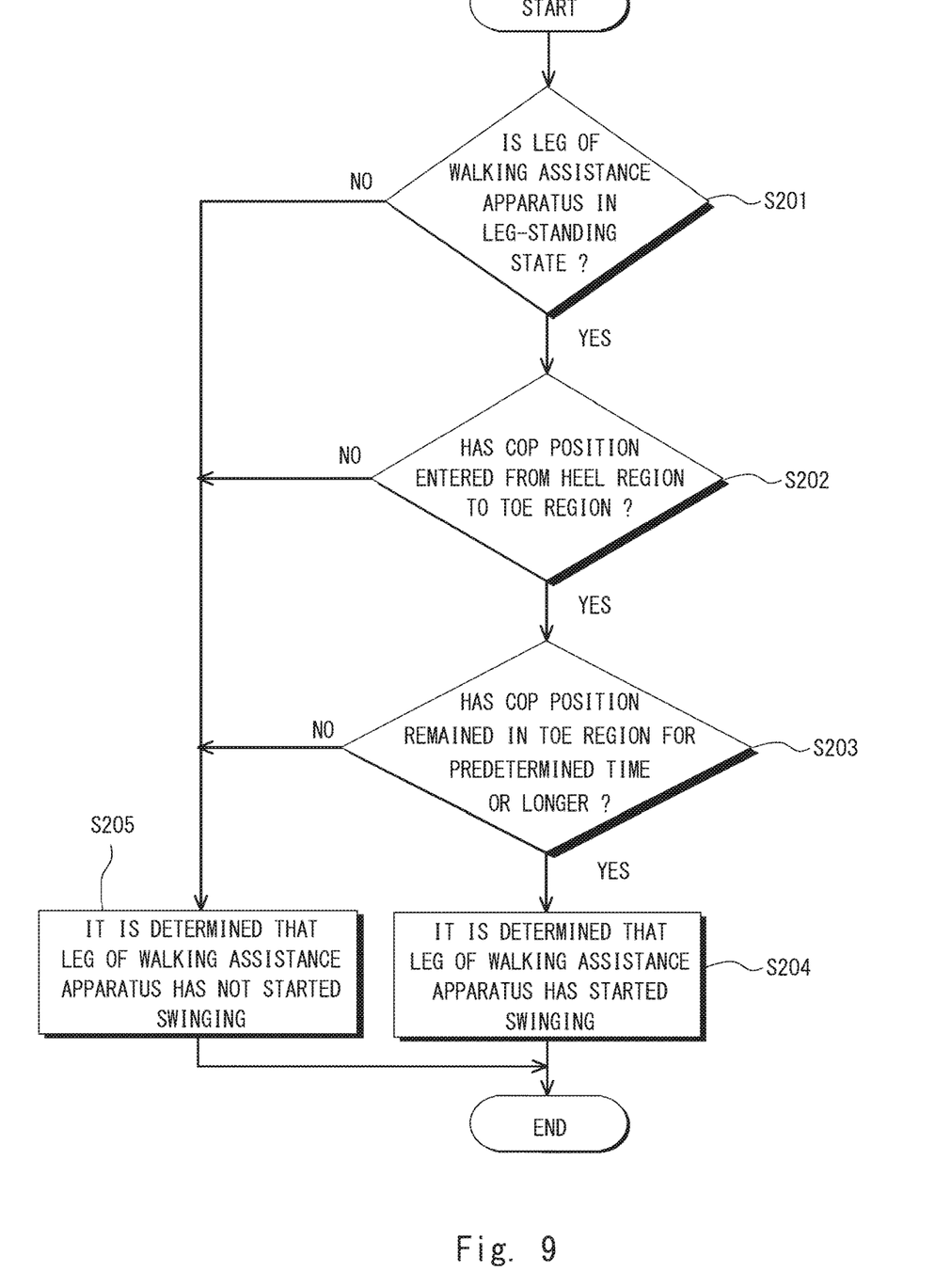
FIG. 9 is a flowchart showing an example of a determination flow according to a gait state determination method.

FIG. 9 is a flowchart showing an example of a determination flow according to the above-described gait state determination method.

The motion determination unit 357 determines whether or not the leg to which the walking assistance apparatus 2 is attached is in a leg-standing state based on the pressure on the sole of the sole frame 25 detected by the pressure sensors 28 of the walking assistance apparatus 2 (step S201).

When the motion determination unit 357 determines that the leg to which the walking assistance apparatus 2 is attached is in the leg-standing state (Yes at step S201), the motion determination unit 357 determines whether or not the COP position $x_{cop}$ has changed from a value smaller than the heel-region determination threshold to a value equal to or greater than the toe-region determination threshold (step S202). On the other hand, when the motion determination unit 357 determines that the leg to which the walking assistance apparatus 2 is attached is not in the leg-standing state (No at step S201), the motion determination unit 357 proceeds to a later-described step S205.

When the motion determination unit 357 determines that the COP position $x_{cop}$ has changed from a value smaller than the heel-region determination threshold to a value equal to or greater than the toe-region determination threshold (Yes at step S202), the motion determination unit 357 determines whether or not the COP position $x_{cop}$ continuously has a value equal to or greater than the toe-region determination threshold (i.e., has remained in the toe region) for a predetermined time or longer (step S203). On the other hand, when the motion determination unit 357 determines that the COP position $x_{cop}$ has not changed from a value smaller than the heel-region determination threshold to a value equal to or greater than the toe-region determination threshold (No at step S202), the motion determination unit 357 proceeds to a later-described step S205.

Figure 10:
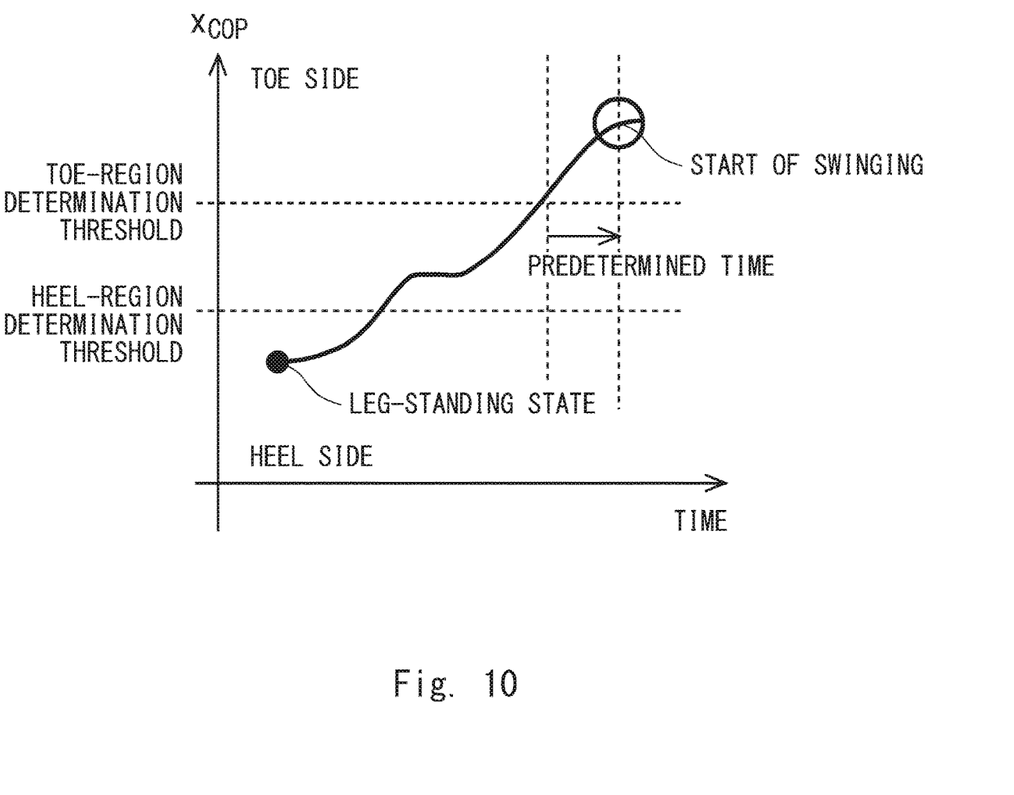
FIG. 10 shows an example of a timing of a start of swinging of a leg.

For example, as shown in FIG. 10, when the motion determination unit 357 determines that the COP position $x_{cop}$ continuously has a value equal to or greater than the toe-region determination threshold for the predetermined time or longer (Yes at step S203), the motion determination unit 357 determines that the user has started swinging his/her leg to which the walking assistance apparatus 2 is attached forward (step S204). On the other hand, when the motion determination unit 357 determines that the COP position $x_{cop}$ does not continuously have a value equal to or greater than the toe-region determination threshold for the predetermined time or longer (No at step S203), the motion determination unit 357 determines that the user has not started swinging his/her leg to which the walking assistance apparatus 2 is attached forward (step S205).

Typically, the pulling force calculation unit 358 controls the first pulling unit 33 so that the vertically-upward component f2 of the pulling force f applied by the first pulling unit 33 reduces the gravitational force of the walking assistance apparatus. For example, the pulling force calculation unit 358 controls the first pulling unit 33 so that the vertically-upward component f2 of the pulling force f applied by the first pulling unit 33 is made equal to the gravitational force of the walking assistance apparatus or equal to half of the gravitational force of the walking assistance apparatus.

Further, when the motion determination unit 357 determines that the user has started swinging his/her leg to which the walking assistance apparatus 2 is attached, the pulling force calculation unit 358 controls the first pulling unit 33 so that the first pulling unit 33 increases its pulling force f.

As described above, according to this exemplary embodiment, the load on the user's walking caused by the gravitational force of the walking assistance apparatus 2 can be reduced by controlling the first pulling unit 33 so that the vertically-upward component f2 of the pulling force f applied by the first pulling unit 33 reduces the gravitational force of the walking assistance apparatus 2. Further, according to this exemplary embodiment, the start of swinging of the leg is accurately determined. Then, the pulling force f1 applied by the first pulling unit 33 is increased and hence its horizontally-forward component f1 is increased at this determined start of swinging of the leg, so that the load caused by the inertial force of the walking assistance apparatus 2 can be reduced at the start of swinging of the leg.

The pulling force calculation unit 358 calculates a pulling force command value for the first pulling unit 33 and outputs the calculated pulling force command value to the first pulling unit 33. The first pulling unit 33 pulls the wire 36 of the walking assistance apparatus 2 according to the pulling force command value output from the pulling force calculation unit 358. At this point, the vertically-upward component f2 of the pulling force f applied by the first pulling unit 33 supports the weight of the walking assistance apparatus 2. The horizontally-forward component f1 of the pulling force f applied by the first pulling unit 33 assists the start of swinging of the leg. That is, the pulling force command value is set so that, for the normal walking motion of the user, the vertically-upward component f2 of the pulling force f supports the weight of the walking assistance apparatus 2 and the horizontally-forward component f1 of the pulling force f optimally assists the start of swinging of the leg.

The pulling force calculation unit 358 sharply increases the pulling force command value in a short time, for example, in a pulsed manner according to the determination of the start of swinging of the leg made by the motion determination unit 357. Note that the increment of the pulling force command value may be set, for example, based on the inertial force of the walking assistance apparatus 2 calculated from the moving speed of the belt 311 of the treadmill 31. When a certain time has elapsed after the start of swinging of the leg is detected, the pulling force calculation unit 358 outputs the normal pulling force command value to the first pulling unit 33.

As described above, in this exemplary embodiment, a pressure exerted on the sole of the sole frame 25 of the walking assistance apparatus 2 is detected and a COP position on the sole is calculated based on the detected pressure on the sole. Then, when the calculated COP position is shifted from a position in a heel region of the sole to a toe region thereof, it is determined that it is a timing of a start of forward swinging of the leg to which the walking assistance apparatus 2 is attached. In this way, it is possible to accurately determine the start of swinging of the leg to which the walking assistance apparatus 2 is attached by using the ergonomic characteristic that the COP position is shifted from the heel region to the toe region when the leg starts swinging. Further, it is possible to reduce the load caused by the inertial force of the walking assistance apparatus 2 and thereby reduce the load exerted on the leg at the start of swinging of the leg, which is accurately determined, by increasing the pulling force f applied by the first pulling unit 33 at the start of swinging of the leg.

Note that the present disclosure is not limited to the above-described exemplary embodiments, and various modifications can be made without departing from the spirit and scope of the present disclosure.

In the above-described exemplary embodiment, the walking assistance apparatus 2 calculates a COP position based on the pressure on the sole of the sole frame 25 detected by the pressure sensors 28 and transmits the calculated COP position to the control device 35. However, the present disclosure is not limited to such a configuration. The computer 355 of the control device 35 may calculate the COP position based on the pressure on the sole of the sole frame 25 detected by the pressure sensors 28 of the walking assistance apparatus 2.

In the above-described exemplary embodiment, the computer 355 of the control device 35 includes the motion determination unit 357 that determines the start of swinging of a leg to which the walking assistance apparatus 2 is attached. However, the present disclosure is not limited to such a configuration. The walking assistance apparatus 2 may include the motion determination unit 357. In this case, when the motion determination unit 357 of the walking assistance apparatus 2 determines the start of swinging of the leg, the pulling force calculation unit 358 of the computer 355 of the control device 35 increases the pulling force command value according to the swinging start determination result received from the motion determination unit 357 of the walking assistance apparatus.

In the above-described exemplary embodiment, the pulling force calculation unit 358 may change the increment of the pulling force command value according to the magnitude of the toe-region determination threshold of the motion determination unit 357 at the time of the determination of the start of swinging of the leg. For example, there are cases where it is desired to reduce the inertial force at the time of the start of swinging of the leg at an early timing and hence the toe-region determination threshold is set to a value smaller than the ordinary value. In such cases, the pulling force calculation unit 358 may reduce the increment of the pulling force command value at the time of the determination of the start of swinging of the leg. On the contrary, there are cases where it is desired to reduce the inertial force at the time of the start of swinging of the leg at a late timing and hence the toe-region determination threshold is set to a value larger than the ordinary value. In such cases, the pulling force calculation unit 358 may increase the increment of the pulling force command value at the time of the determination of the start of swinging of the leg. In this way, the inertial force at the time of the start of swinging of the leg can be reduced in a more natural manner.

In the above-described exemplary embodiment, the pulling force calculation unit 358 may increase the pulling force command value according to the determination of the start of swinging of the leg made by the motion determination unit 357 and then gradually decrease the pulling force command value. For example, the pulling force calculation unit 358 increases the pulling force command value in a pulsed manner when the start of swinging of the leg is determined. After that, the pulling force calculation unit 358 gradually decreases the pulling force command value and returns the pulling force command value to the normal value when the swinging period has been finished (when the sole frame 25 lands on the ground). In this case, the pulling force calculation unit 358 may increase the pulling force command value as the pulling force exerted on the wire 36 of the walking assistance apparatus 2 increases during this swinging period.

In this way, it is possible to continuously add a pulling force larger than the normal pulling force in the swinging direction during the swinging period. As a result, it is possible to reduce not only the load caused by the inertial force but also the overall load of the swinging motion.

The above-described exemplary embodiment may have a configuration in which a third pulling unit that pulls the walking assistance apparatus upward and backward through a wire is provided in the crosswise frame 323 of the frame main body 32. The third pulling unit is a specific example of the second pulling means. The resultant force of the vertically-upward components of the pulling forces applied by the first and third pulling units supports the weight of the walking assistance apparatus 2. Further, the resultant force of the horizontal components of the pulling forces applied by the first and third pulling units assists the start of swinging of the leg.

The pulling force calculation unit 358 outputs a pulling force command value that makes the resultant force of the vertically-upward components of the pulling forces applied by the first and third pulling units equal to the gravitational force of the walking assistance apparatus 2 to the first and third pulling units. Further, the pulling force calculation unit 358 increases the pulling force command value from its normal value for a certain time period according to the determination of the start of swinging of the leg made by the motion determination unit 357 and outputs the increased pulling force command value to the first pulling unit 33. At this point, the pulling force calculation unit 358 is outputting the normal pulling force command value (pulling force command value=constant) to the third pulling unit. However, the present disclosure is not limited to such a configuration and method.

That is, the pulling force command value for the third pulling unit may be changed in a manner similar to the pulling force command value for the first pulling unit 33. In other words, the pulling force calculation unit 358 changes the pulling force command values for the first and third pulling units and thereby increases the horizontally-forward components of the pulling forces applied by the first and third pulling units at the start of swinging of the leg. In this way, the vertically-upward components and the horizontally-forward components of the pulling forces applied by the first and third pulling units can be accurately controlled independently of each other. As a result, it is possible to, while reducing the load caused by the gravitational force of the walking assistance apparatus, reduce the load exerted on the leg to which the walking assistance apparatus 2 is attached at the start of swinging of that leg in a more optimal manner.

In the above-described exemplary embodiment, the training apparatus 3 may not include the frame main body 32. In such a case, the first and second pulling units may be, for example, disposed (or mounted) on the wall or the ceiling.

Although the wire 36 of the first pulling unit 33 is connected to the walking assistance apparatus 2 in the above-described exemplary embodiment, the present disclosure is not limited to such a configuration. For example, the wire 36 of the first pulling unit 33 may be connected to the user's leg through a fixture such as a belt and ring. Further, the wire 36 of the first pulling unit 33 may be connected to both the walking assistance apparatus 2 and the user's leg.

Although the user outfitted with the walking assistance apparatus 2 walks on the treadmill 31 in the above-described exemplary embodiment, the present disclosure is not limited to such a configuration. The present disclosure may be applied to a configuration in which a user outfitted with the walking assistance apparatus 2 walks on a stationary road surface and the first pulling unit 33 is moved according to the movement of the user.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A walking training apparatus comprising:
a gait state determination apparatus that determines a gait state of a user with a walking assistance apparatus attached to a leg of the user, the walking assistance apparatus being configured to assist the user to walk, the gait state determination apparatus comprising:
  a foot attachment structure disposed in the walking assistance apparatus, the foot attachment structure to be attached to a foot of the user:
  a pressure detector, disposed in the foot attachment structure, configured to detect a pressure exerted on a sole of the user; and
  a processor that
    successively calculates a center position of a pressure exerted on the sole during a gait motion of the user based on the pressure exerted on the sole detected by the pressure detector; and
    determines that a time when the calculated center position of the pressure is shifted from a position in a heel region of the sole to a toe region thereof, is a time of a start of forward swinging of the leg to which the walking assistance apparatus is attached, the time beinn when the calculated center position of the pressure has changed from a value smaller than a heel-region determination threshold to a value equal to or greater than a toe-region determination threshold; and
  first pulling means for pulling the leg upward and forward directly or through the walking assistance apparatus,
  wherein the processor is configured to control the first pulling means so that a vertically-upward component of a pulling force applied by the first pulling means reduces a weight of the walking assistance apparatus,
  wherein the processor is configured to make the first pulling means generate an additional pulling force in addition to the pulling force at the time of the start of forward swinging of the leg to which the walking assistance apparatus is attached, and
  wherein the processor is configured to change a magnitude of the additional pulling force according to a magnitude of the toe-region determination threshold.

2. The walking training apparatus according to claim 1, wherein the processor is configured to determine that it is the time of the start of forward swinging of the leg to which the walking assistance apparatus is attached when the center position of the pressure is shifted from the heel region of the sole to the toe region thereof and remains in the toe region for a predetermined time or longer.

3. A walking training method comprising:
determining a gait state of a user with a walking assistance apparatus attached to a leg of the user, the walking assistance apparatus being configured to assist the user to walk, the determining the gait state of the user comprising:
  detecting a pressure exerted on a sole of a foot of the leg to which the walking assistance apparatus is attached;
  successively calculating a center position of a pressure exerted on the sole during a gait motion of the user based on the pressure exerted on the sole detected; and
  determining that a time when the calculated center position of the pressure is shifted from a position in a heel region of the sole to a toe region thereof, is a time of a start of forward swinging of the leg to which the walking assistance apparatus is attached, the time being when the calculated center position of the pressure has changed from a value smaller than a heel-region determination threshold to a value equal to or greater than a toe-region determination threshold;
providing a first pulling mechanism for pulling the leg upward and forward directly or through the walking assistance apparatus;
controlling the first pulling mechanism so that a vertically-upward component of a pulling force applied by the first pulling mechanism reduces a weight of the walking assistance apparatus;
making the first pulling mechanism generate an additional pulling force in addition to the pulling force at the time of the start of forward swinging of the leg to which the walking assistance apparatus is attached; and
changing a magnitude of the additional pulling force according to a magnitude of the toe-region determination threshold.

4. The walking training method according to claim 3, wherein the time of the start of forward swinging of the leg to which the walking assistance apparatus is attached is determined when the center position of the pressure is shifted from the heel region of the sole to the toe region thereof and remains in the toe region for a predetermined time or longer.

5. A walking training apparatus comprising:
a gait state determination apparatus that determines a gait state of a user with a walking assistance apparatus attached to a leg of the user, the walking assistance apparatus being configured to assist the user to walk, the gait state determination apparatus comprising:
  a foot attachment structure disposed in the walking assistance apparatus, the foot attachment structure to be attached to a foot of the user;

a pressure sensor disposed in the foot attachment structure, the pressure sensor configured to detect a pressure exerted on a sole of the user; and circuitry configured to:
  successively calculate a center position of a pressure exerted on the sole during a gait motion of the user based on the pressure exerted on the sole detected by the pressure sensor, and
  determine that a time when the calculated center position of the pressure is shifted from a position in a heel region of the sole to a toe region thereof, is a time of a start of forward swinging of the leg to which the walking assistance apparatus is attached, the time being when the calculated center position of the pressure has changed from a value smaller than a heel-region determination threshold to a value equal to or greater than a toe-region determination threshold; and a first pulling mechanism to pull the leg upward and forward directly or through the walking assistance apparatus, wherein the circuitry is further configured to:
  control the first pulling mechanism so that a vertically-upward component of a pulling force applied by the first pulling mechanism reduces a weight of the walking assistance apparatus,
  make the first pulling mechanism generate an additional pulling force in addition to the pulling force at the time of the start of forward swinging of the leg to which the walking assistance apparatus is attached, and
  change a magnitude of the additional pulling force according to a magnitude of the toe-region determination threshold.

6. The walking training apparatus according to claim 5, wherein the circuitry is configured to determine that it is the time of the start of forward swinging of the leg to which the walking assistance apparatus is attached when the center position of the pressure is shifted from the heel region of the sole to the toe region thereof and remains in the toe region for a predetermined time or longer.

* * * * *